(12) United States Patent
Diguet et al.

(10) Patent No.: US 8,927,046 B2
(45) Date of Patent: Jan. 6, 2015

(54) RESVERATROL COMPOSITIONS

(75) Inventors: Sylvain Diguet, Hagenthal-le-haut (FR);
Nicolle Goetz, Waldshut-Tiengen (DE);
Bruno H. Leuenberger, Rheinfelden (CH); Johann Ulm, Oberwil (CH); Loni Schweikert, Zuzgen (CH)

(73) Assignee: DSM IP Assets B.V., Heerlen (NL)

( * ) Notice: Subject to any disclaimer, the term of this patent is extended or adjusted under 35 U.S.C. 154(b) by 229 days.

(21) Appl. No.: 13/147,885

(22) PCT Filed: Feb. 3, 2010

(86) PCT No.: PCT/EP2010/000665
§ 371 (c)(1),
(2), (4) Date: Oct. 18, 2011

(87) PCT Pub. No.: WO2010/089104
PCT Pub. Date: Aug. 12, 2010

(65) Prior Publication Data
US 2012/0045563 A1    Feb. 23, 2012

(30) Foreign Application Priority Data
Feb. 4, 2009   (EP) .................................... 09152064

(51) Int. Cl.
*A23L 1/025*    (2006.01)
*A23L 1/0522*   (2006.01)
*A23L 1/09*     (2006.01)
*A61K 9/00*     (2006.01)
*A61K 9/16*     (2006.01)
*A61K 9/20*     (2006.01)
*A61K 31/05*    (2006.01)
*A61K 9/46*     (2006.01)

(52) U.S. Cl.
CPC ............. *A61K 9/1652* (2013.01); *A61K 9/0095* (2013.01); *A61K 9/1658* (2013.01); *A61K 9/1623* (2013.01); *A61K 9/2077* (2013.01); *A61K 31/05* (2013.01); *A61K 9/0007* (2013.01)
USPC ........... 426/648; 426/506; 426/518; 426/573; 426/576; 426/578; 426/590; 426/654

(58) Field of Classification Search
USPC ......... 426/648, 654, 573, 576, 578, 506, 518, 426/590
See application file for complete search history.

(56) References Cited

FOREIGN PATENT DOCUMENTS

| | | |
|---|---|---|
| EP | 1 844 784 | 10/2007 |
| JP | 2006-528950 | 12/2006 |
| JP | 2008-542296 | 11/2008 |
| MD | 2659 B1 | 1/2005 |
| WO | WO 03/097012 | 11/2003 |
| WO | WO 2004/105517 | 12/2004 |
| WO | WO 2006/127987 | 11/2006 |
| WO | WO 2007/009997 | 1/2007 |
| WO | WO 2007/045488 | 4/2007 |
| WO | WO 2007/088046 | 8/2007 |

OTHER PUBLICATIONS

International Search Report for PCT/EP2010/000665, mailed Nov. 22, 2010.
Frömming et al, "*Cyclodextrins in Pharmacy*", ISBN 0-7923-2139-1, p. 217 (1994).
Amri et al; "*Administration of resveratrol: What formulation solutions to bioavailability limitations?*", Journal of controlled Release 158 (2012) 182-193.

*Primary Examiner* — Helen F Heggestad
(74) *Attorney, Agent, or Firm* — Nixon & Vanderhye P.C.

(57) ABSTRACT

Compositions consisting of or comprising resveratrol and a protective colloid, particularly a gelatine, a modified food starch or a ligninsulfonate, their use for stably incorporating resveratrol into water-based foods, particularly beverages, and the foods thus obtained.

20 Claims, No Drawings

RESVERATROL COMPOSITIONS

This application is the U.S. national phase of International Application No. PCT/EP2010/000665 filed 3 Feb. 2010 which designated the U.S. and claims priority to EP Patent Application No. 09152064.3 filed 4 Feb. 2009, the entire contents of each of which are hereby incorporated by reference.

The present invention relates to compositions consisting of as well as comprising resveratrol and a protective colloid, particularly a gelatine or a modified food starch. The present invention further relates to processes for the preparation of such compositions and their use in dietary supplements and water-based food, particularly in beverages. The present invention also relates to the use of a protective colloid, particularly a gelatine or a modified food starch for increasing the solubility or suspensibility of resveratrol in water or aqueous solutions.

Resveratrol, 3,5,4'-trihydroxystilbene or 5-[2-(4-hydroxyphenyl)-ethenyl]-1,3-benzenediol, is a phytoalexin. Phytoalexins are produced naturally by several plants as a defense against infections by pathogens such a bacteria and fungi. A number of beneficial health effects of resveratrol, especially of trans-resveratrol, on animals, particularly human beings, have been reported, such as anti-cancer, antiviral, neuroprotective anti-aging, anti-inflammatory and life-prolonging effects. Therefore, the demand for resveratrol and application forms is constantly increasing. In this connection the relatively low solubility of resveratrol in water, especially in cold water, is a limiting factor for some of its uses and causes problems.

Several solutions of solving this problem, i.e. of increasing the water-solubility of resveratrol, have been suggested and described.

WO 2005/000258 discloses self-assembled nanoparticles comprising an amphiphilic polymer consisting of polycaprolactone and polyethyleneglycol solubilizing and entrapping a physiologically active ingredient, e.g., resveratrol in aqueous solutions. These nanoparticles are useful in therapeutic and cosmetic external applications to the skin.

WO 2007/146318 discloses non-alcoholic and alcoholic retail beverages comprising resveratrol in amounts of 5-300 mg/l and 15 mg/l-2.5 g/l, respectively, preferably 10-30 mg/l and 50-750 mg/l, respectively, and vitamins A, C or E as stabilizing agents.

There is, however, still a need to have available additional physiologically compatible compounds capable of increasing the solubility or suspensibility of resveratrol in water, particularly in cold water, or corresponding aqueous solutions. It has been found surprisingly that this objective is achieved by compositions consisting of or comprising resveratrol and a protective colloid. Such compositions of the present invention are hereinafter designated "resveratrol CWS".

The term "resveratrol" relates to resveratrol with trans- and cis-configuration and includes cis/trans mixtures. Particularly preferred is trans-resveratrol which may contain minor amounts of the cis isomer. The resveratrol can be of whatever origin, e.g., be of natural origin, i.e., extracted from natural sources, concentrated and purified, or synthetically prepared. Natural sources comprise animal, plants or microorganisms which are genetically manipulated to produce or overproduce resveratrol. The resveratrol may be in crystalline or amorphous form and may have been treated to improve its flowability. Synthetically prepared resveratrol is preferred, especially in crystalline form, in view of its high purity and safety in food and dietary applications. On the other hand concentrated and purified extracts from natural sources are prefer-red which contain additional pharmacologically active and valuable components, e.g. other phenolic compounds, increasing or even potentiating the beneficial effects of resveratrol.

The term "protective colloid" encompasses gelatine (from any origin, e.g., pigs, cattle, poultry or fish), plant gums (such as gum arabic or gum acacia) and plant proteins (e.g., from soy-bean, pea, rice, lupin), ligninsulfonates (particularly in food-grade quality) and food starches (from any origin, preferably in modified form). Examples and preferred embodiments of modified food starches are OSA (octenyl succinic acid anhydride) modified starches, commercially available under several well-known trade marks, e.g., Capsul S.

The weight amount of resveratrol in the compositions consisting of or comprising resveratrol and a protective colloid of the present invention is in the range of 1-80%, 2-70%, 3-60%, 4-50% and, preferably, 5-20%.

The weight amount of the protective colloid in the compositions is in the range of 20-99%, 30-98%0, 40-97%, 50-96% and preferably 80-95%.

Ingredients which may be optionally present in the compositions of the present invention are those known to a person skilled in the art to be normally present in such compositions and are selected from the group consisting of but not restricted to sugars, artificial sweeteners, antioxidants, colorants, flavourings and flavour enhancers, PEG, casein, pectin, effervescent powders, excipients and adjuvants which are compatible with the main components.

The compositions can be in the form of aqueous suspensions or of dry powders to including beadlets and granules. While in simple powders the main components, resveratrol and protective colloid, and optional further components are present as a mixture of fine particles (as "solid dispersion") in case of beadlets and granules the resveratrol particles are completely or partially coated with or embedded in the protective colloid. If desired, the powders may finally be brought into a suitable galenical form, e.g. tablets, with or without the use of suitable adjuvants or excipients. Such galenical forms, including tablets and appropriate dosage units are made in accordance with methods well-known to persons skilled in the art.

The preferred particle size distribution of the compositions in form of powders including beadlets and granules is as follows:

At least 95% of the particles have a size of ≤1500 μm (preferably ≤1000 μm, more preferably ≤850 μm), with at most 35% of the particles having a size of ≤50 μm (preferably ≤100 μm, more preferably ≤150 μm).

In another preferred embodiment of the present invention particle size distribution of the composition of the present invention, preferably in form of a powder or of granules, is as follows:

At least 95% of the particles have a size of ≤1500 μm (preferably ≤1000 μm, more preferably ≤850 μm), with at most 35% of the particles having a size of 510 μm (preferably ≤20 μm, more preferably ≤50 μm).

The compositions according to the present invention when being in the form of dry powders including beadlets and granules may still contain some water and have preferably a water activity of from 0.05 to 0.7, preferably of from 0.1 to 0.5, more preferably of from 0.2 to 0.5. The water activity is measured using a Novasina Thermoconstanter TH200 (Novasina AG, Zürich, Switzerland).

According to the present invention it is advantageous if the moisture content in the powder or granule compositions is in the range of from 0 to 8 weight-%, preferably from 0 to 6 weight-%, each based on the total weight of the composition.

When the resveratrol in the compositions of the present invention is in crystalline form, the resveratrol crystals have needle dimensions within the following ranges: length (L): 200 to 800 μm, preferably 100 to 400 μm; thickness (D): 5 to 100 μm and form factor (L/D): 5 to 30. Crystals with these dimensions are obtained before milling. By milling in appropriate mills well-known in the art, the dimensions of the resveratrol crystals in the compositions of the present invention can be reduced. The lower the particle size of the crystalline resveratrol to be obtained is the more recommendable is wet-milling which can be done in water or a water/organic solvent mixture, the organic solvent being a lower alkanol or lower alkanoic acid ester, preferably ethanol or ethyl acetate, respectively. Preferably, the resveratrol crystals in the compositions of the present invention have a Malvern particle size d50 between 0.05 and 10 μm, more preferably between 0.1 and 2 μm after the milling.

In a further aspect, the present invention relates to processes for the manufacture of the compositions of the present invention.

Manufacture of the Compositions:

The compositions of this invention may be produced by any method known per se for the production of aqueous suspensions and powders including granules and beadlets, e.g., described for the preparation of similar compositions comprising hydrophobic/lipophilic components such as edible oils, carotenoids, fat-soluble vitamins (A, D, E, K), coenzymes Q, PUFAs and their esters and solubility enhancers, stabilizers or protective colloids. Preferred methods are fluidized-bed granulation, high-shear granulation, extrusion, spray-drying and wet granulation of aqueous suspensions as described, e.g. in EP 0 498 824 and EP 1 940 249.

For obtaining powder compositions of the present invention by spray-drying it is convenient to prepare a slurry of all components in a solvent or solvent mixture which is able to dissolve the protective colloid. An especially preferred solvent is water. The slurry has preferably a solid content of 10 to 70% by weight, preferably of 25 to 50% by weight, each based on the total weight of the slurry. The slurry is then spray-dried in a manner known per se. Instead of spray-drying the aqueous slurries or suspensions they can be directly used in the preparation of beverages dairy products fortified with resveratrol to desired concentrations.

Thus another aspect of the present invention is a process for the manufacture of a composition as mentioned above, which comprises preparing a slurry, preferably an aqueous slurry, of all solid components, preferably having a solid content of 10 to 70% by weight, preferably 25 to 50% by weight, each based on the total weight of the slurry, and drying the slurry in a manner known per se, e.g., by spray cooling and drying to the desired water content in a fluidized bed or by modified spray drying at higher temperatures.

Alternatively, the slurry may be sprayed onto starch powder and the beadlets obtained be dried at relatively low temperature, e.g., about 60° C.

Spray-granulation is an especially preferred process for the manufacture of the compositions of the present invention.

At the end of the granulation process, the granules may be sieved to fractionate the granules as to size. While the particle size is not narrowly critical to the invention it is, for practical purposes, preferably within 50 and 1500 μm, more preferably between 100 and 1000 μm, most preferably from 150 to 850 μm.

A representative method of preparing the compositions of the present invention is as follows:

The matrix is prepared by dissolving deionised water at 60° C. and adding the protective colloid and the sugar. The dissolution time is generally 60 minutes. Then an antioxidant and the resveratrol crystals are added and stirred. The antioxidant, however, can also be added after the wet-milling step (see below). Optionally some other additives like oils or glycerin and some surfactants like ascorbyl palmitate, polyethyleneglycol or sucroester are added and the mixture is stirred. The stirred suspension is then passed through a ball mill (wet-milling) for 1 to 6 hours. After the milling step, the resveratrol has an average particle size which is lower than before and is preferably between 0.05 and 2 microns, more preferably between 0.1 and 1 micron. Preferred is that the suspension is then dried using either a spray drying technology if possible with agglomeration to obtain granules or the beadlet technology as described, e.g., in EP 1 940 249, preferably in form of a powder-catch process. But it is also possible to use the suspension as liquid form of a composition according to the present invention, preferably after stabilization with preservatives.

It has been found that the close control of the particle size after the wet-milling step is key for the dissolution kinetic and for the bioavailability. At 80° C. in water, resveratrol crystals need more than 15 minutes to dissolve completely to reach a concentration of 120 mg/liter. The resveratrol dissolved at 80° C. will then crystallize and make deposits within a couple of days at room temperature (see Reference before the examples below). After the milling, the resveratrol CWS is dissolved within 1 minute at 80° C. 1 minute at 80° C. are standard conditions for the pasteurization step for the production of the beverages. This dissolution of the resveratrol during this pasteurization step ensures a good physical stability of the resveratrol in the beverages.

The compositions of the present invention provide a higher suspensibility of resveratrol in aqueous solutions even when the viscosity of the aqueous solution is low thus allowing it to be incorporated into water-based food, particularly beverages, in higher concentrations achieving a higher bioavailability and low turbidity. By using the compositions of the present invention resveratrol can be stably solved or suspended in aqueous solutions, particularly cold solutions, of up to 100 mg/l and higher. The term "cold" in this connection relates to solutions with temperatures as in refrigerators up to room temperature, e.g., from 5° C. to 25° C., preferably below room temperature.

Therefore, a further aspect of the present invention are applications of the new compositions in water-based foods to achieve a stable supplementation of such foods with resveratrol. These foods comprise those products wherein it is essential to avoid a segregation or sedimentation of resveratrol, i.e., especially in beverages and dairy products. By use of the present compositions a stable supplementation with resveratrol of water-based foods, particularly beverages, is achieved over a pH range from about 2.5 to 7 for at least 6 months and up to 9 months or more. Pasteurization of the final product can improve the stability thereof, in case of beverages markedly. Tablets or powder compositions comprising effervescent powders, e.g., bicarbonates, are preferred by end users for fortification of beverages immediately before consumption.

Beverages include non-alcoholic and alcoholic beverages which may be carbonated, flavoured and/or coloured. Examples are mineral waters, seltzers, soft drinks, energy drinks, cola drinks, coffees, teas, fruit and vegetable juices in concentrated or diluted form and all kinds of beers and wines. Examples of dairy products are all kinds of milk including concentrates and milk powders, all kinds of yoghurts and whey.

The desired concentration of resveratrol in the food products can vary within wide ranges and is normally, depending upon the nature of the product, in the range of 50 mg/l to 1000 mg/l. Optimization of the respective amount can be easily found out by the person skilled in the art and specialized in this business.

The present invention, therefore, is also related to the water-based foods which have been supplemented by the compositions of the present invention themselves, to a method for their preparation, to the use of these compositions for the stable supplementation of water-based food with resveratrol and for the use of the protective colloids defined hereinbefore, particularly of gelatins and modified food starches, in the preparation of the compositions of the present invention.

The stable supplementation of water-based food with resveratrol or the process of stably incorporating resveratrol into such food, particularly into beverages, by use of the present compositions is achieved in accordance with methods known per se. The compositions are, e.g., added to the food at a suitable stage in its production process, be it as the final step before packaging or at an earlier step, e.g., before pasteurization, and distributed therein to form a homogeneous suspension. The product may then be further processed in accordance with known methods.

The invention is described in more detail and illustrated by the following examples.

Reference

Different concentration of Resvida™ (resveratrol cryst.) not milled were dispersed in mineral drink water (Arkina) and pasteurized at 80° C. for 1 minute. The following results with trans-resveratrol suspended in water (analysis done with HPLC) have been obtained:

| Theoretical Concentration | Concentration initial | Concentration after 18 hours | Concentration after 5 days | Observation |
|---|---|---|---|---|
| 81.5 mg/liter | 71.8 mg/liter | 62.0 mg/liter | 65.0 mg/liter | Deposits + |
| 98.5 mg/liter | 87.4 mg/liter | 67.0 mg/liter | 47.1 mg/liter | Deposits ++ |
| 119 mg/liter | 102.6 mg/litre | 67.7 mg/liter | 55.5 mg/liter | Deposits +++ |
| 160 mg/liter | 123.7 mg/liter | 67.5 mg/liter | 46.4 mg/liter | Deposits +++ |
| 205.5 mg/liter | 142.0 mg/liter | 61.3 mg/liter | 40.5 mg/liter | Deposits ++++ |

EXAMPLE 1

330 g of deionised water was heated up at 60° C. 118.2 g of fish gelatine and 118.2 g of sucrose were added to the water and dissolved 1 hour at 60° C. 3.6 g of dl-alpha tocopherol and 40 g of crystalline resveratrol (Malvern particle size d50 between 100 and 300 microns) were then added. The mixture was milled in a wet mill for 1 hour at 60° C. with a rotation speed of 4000 rpm. After the milling the resveratrol had a Malvern particle size d50 between 0.1 and 1 micron.

250 g of the obtained suspension was sprayed in fluidized corn starch. The obtained beadlets were dried in a Retsch fluid bed at 60° C. under vacuum (500 mbar) for 30 minutes.

The final product had the following composition (w/w):

| | |
|---|---|
| resveratrol | 10.07% |
| fish gelatine | 26.13% |
| sucrose | 29.74% |
| dl-alpha tocopherol | 0.91% |

-continued

| | |
|---|---|
| water | 3.15% |
| starch | 30.00% |

EXAMPLE 2

432 g of deionised water was heated up at 60° C. 141.8 g of fish gelatine and 141.8 g of sucrose a were added to the water and dissolved 1 hour at 60° C. 4.3 g of dl-alpha tocopherol and 54 g of crystalline resveratrol (Malvern particle size d50 between 100 and 130 microns) were then added. The mixture was milled in a wet mill for 1 hour at 60° C. with a rotation speed of 4000 rpm. After milling, the resveratrol had a Malvern particle size d50 between 0.1 and 1 micron.

202 g of the obtained suspension was sprayed in fluidized corn starch. The obtained beadlets were dried in a Retsch fluid bed for 2 hours at 30° C. and for 1 hour at 40° C.

The final product had the following composition (w/w):

| | |
|---|---|
| resveratrol | 11.60% |
| fish gelatine | 26.74% |
| sucrose | 30.45% |
| dl-alpha tocopherol | 0.92% |
| water | 6.15% |
| starch | 24.13% |

Retention of resveratrol after 3 and 12 months at 25° C., 60% relative humidity (sealed aluminium bags) was 99% and 105%, respectively, and after 3 and 12 months at 40° C., 75% relative humidity (sealed aluminium bags) was 103% and 104%, respectively. Values higher than 100% are due to the determination method and mean that no loss of resveratrol could be determined.

EXAMPLE 3

280 g of deionised water was heated up at 60° C. 141.8 g of capsule S and 141.8 g of sucrose were added to the water and dissolved 1 hour at 60° C. 4.3 g of dl-alpha tocopherol and 54 g crystalline resveratrol (Malvern particle size d50 between 100 and 130 microns) were then added. The mixture was milled in a wet mill for 1 hour at 60° C. with a rotation speed of 4000 rpm. After milling, the resveratrol had a Malvern particle size d50 between 0.1 and 1 micron. Deionised water was added to obtain a suspension with a solid content of 47.58%.

198.6 g of the obtained suspension was sprayed in fluidized corn starch. The obtained beadlets were dried in a Retsch fluid bed for 20 minutes at 40° C. and for 10 minutes at 50° C.

The final product had the following composition (w/w):

| | |
|---|---|
| resveratrol | 8.05% |
| Capsul S | 18.99% |
| sucrose | 21.13% |
| dl-alpha tocopherol | 0.64% |
| water | 6.11% |
| starch | 45.08% |

Retention of resveratrol after 3 and 12 months at 25° C., 60% relative humidity (sealed aluminium bags) was 104% and 103%, respectively, and after 3 months at 40° C., 75% relative humidity (sealed aluminium bags) was 103% and 101%, respectively. Values higher than 100% are due to the determination method and mean that no loss of resveratrol could be determined.

EXAMPLE 4

400 g of deionised water was heated up at 60° C. 141.8 g of fish gelatine and 141.8 g of sucrose were added to the water and dissolved 1 hour at 60° C. 8.6 g of dl-alpha tocopherol and 27 g of crystalline resveratrol (Malvern particle size d50 between 100 and 130 microns) were then added. The mixture was milled in a wet mill for 4 hours at 80-90° C. with a rotation speed of 4000 rpm. After milling, the resveratrol had a Malvern particle size d50 between 0.1 and 1 micron.

The aqueous suspension had the following composition (w/w):

| | |
|---|---|
| resveratrol | 3.75% |
| fish gelatine | 17.31% |
| sucrose | 19.72% |
| dl-alpha tocopherol | 1.20% |
| water | 58.02% |

209 g of the obtained suspension was sprayed in fluidized corn starch. The obtained beadlets were dried for 15 minutes at 60° C.

The final product had the following composition:

| | |
|---|---|
| resveratrol | 6.25% |
| fish gelatine | 28.80% |
| sucrose | 32.80% |
| dl-alpha tocopherol | 1.89% |
| water | 6.12% |
| starch | 24.05% |

EXAMPLE 5

452 g of deionised water was heated up at 60° C. 141.8 g of fish gelatine and 141.8 g of sucrose were added to the water and dissolved 1 hour at 60° C. 8.6 g of dl-alpha tocopherol, 31 g of crystalline resveratrol (Malvern particle size d50 between 100 and 130 microns) and 50 g of glycerol were then added. The mixture was milled in a wet mill for 4 hours at 80-90° C. with a rotation speed of 4000 rpm. After milling, the resveratrol ha a Malvern particle size d50 between 0.1 and 1 microns.

213 g of the obtained suspension was sprayed in fluidized corn starch. The obtained beadlets were dried at 60° C. for 15 minutes.

The final product had the following composition (w/w):

| | |
|---|---|
| resveratrol | 5.15% |
| fish gelatine | 20.67% |
| sucrose | 23.54% |
| dl-alpha tocopherol | 1.43% |
| water | 5.63% |
| starch | 35.28% |

EXAMPLE 6

550 g of deionised water was heated up at 60° C. 190 g of fish gelatine and 190 g of sucrose were added to the water and dissolved 1 hour at 60° C. 4.5 g of dl-alpha tocopherol and 50 g of crystalline resveratrol (Malvern particle size d50 between 100 and 130 microns) were then added. The mixture was milled in a wet mill for 3 hours at 60° C. and for 1 hour at 80° C. with a rotation speed of 4000 rpm. After milling, the resveratrol had a Malvern particle size d50 between 0.1 and 1 micron. The suspension thus obtained is "suspension 1".

300 g of deionised water were added to 251.5 g of suspension 1.100 g of the obtained diluted suspension were spray dried in a Büchi Minispray dryer 190 with an inlet air temperature of 180° C.

The final product had the following composition (w/w):

| | |
|---|---|
| resveratrol | 11.38% |
| fish gelatine | 37.98% |
| sucrose | 43.25% |
| dl-alpha tocopherol | 1.02% |
| water | 6.37% |

This powder was dissolved in mineral drink water (Arkina) and pasteurized at 80° C. for 1 minute. The following results with trans-resveratrol suspended in water (analysis done with HPLC) have been obtained:

| Theoretical Concentration | Concentration initial | Concentration after 3 weeks | Observation |
|---|---|---|---|
| 118.4 mg/liter; pH = 3 | 117.5 mg/liter | 116.7 mg/liter | No deposits |
| 119.8 mg/liter; pH = 7 | 118.3 mg/liter | 105.5 mg/liter | No deposits |

2.3 g of ascorbyl palmitate were added to 500 g of suspension 1. The pH was then adjusted to 7.2-7.5 with sodium hydroxide. The obtained suspension is "suspension 2". Then 507.8 g of deionised water were added to 245.5 g of suspension 2.100 g of the obtained diluted suspension were spray dried in a Büchi Minispray dryer 190 with an inlet air temperature of 180° C.

The final product had the following composition:

| | |
|---|---|
| resveratrol | 11.38% |
| fish gelatine | 37.96% |
| sucrose | 43.23% |
| dl-alpha tocopherol | 1.02% |
| ascorbyl palmitate | 1.03% |
| water | 5.38% |

2.3 g of sodium ascorbate were added to 250 g of suspension 2. The thus obtained suspension is "suspension 3". Then, 427 g of deionised water were added to 250 g of suspension 3. 100 g of the obtained diluted suspension were spray dried in a Büchi Minispray dryer 190 with an inlet air temperature of 180° C.

The final product had the following composition (w/w):

| | |
|---|---|
| resveratrol | 11.14% |
| fish gelatine | 37.18% |
| sucrose | 42.34% |
| dl-alpha tocopherol | 1.00% |
| ascorbyl palmitate | 1.01% |
| sodium ascorbate | 2.03% |
| water | 5.29% |

EXAMPLE 7

600 g of deionised water was heated up at 60° C. 280 g of Capsul 5 and 120 g of sucrose were added to the water and dissolved within 1 hour at 60° C. Then 46.8 g of crystalline resveratrol were added. The product was milled in a wet mill with 330 g of ZrO$_2$ beads (diameter 0.4 mm) for 2 hours at 43-46° C. with a rotation speed of 4000 rpm.

Before milling, the resveratrol had a Malvern particle size d50 between 20 and 40 microns. After the milling, the resveratrol had a Malvern particle size d50 between 0.1 and 1 micron. The suspension obtained is suspension 1.

307 g of deionised water was added to 928 g of the suspension 1. The obtained diluted suspension was spray dried in a Niro FSD-0.8 Minor with an inlet air temperature of 150° C.

The final product had the following composition (w/w):

| | |
|---|---|
| resveratrol | 9.73% |
| Capsul S | 58.20% |
| sucrose | 24.93% |
| water | 7.14% |

Retention of resveratrol after 3 months at 25° C., 60% relatively humidity (sealed aluminium bags): 99%.

Retention of resveratrol after 3 months at 40° C., 75% relative humidity (sealed aluminium bags): 100%

EXAMPLE 8

600 g of deionised water was heated up at 60° C. 280 g of calcium ligninsulfonate and 120 g of sucrose were added to the water and dissolved within 1 hour at 60° C. Then 46.8 g of resveratrol crystalline were added. The product was milled in a wet mill with 330 g of ZrO$_2$ beads (diameter 0.4 mm) for 2 hours at 40-45° C. with a rotation speed of 4000 rpm.

Before milling, the resveratrol had a Malvern particle size d50 between 20 and 40 microns. After the milling, the resveratrol had a Malvern particle size d50 between 0.1 and 1 micron. 960 g of the suspension obtained was spray dried in a Niro FSD-0.8 Minor with an inlet air temperature of 130° C.

The final product had the following composition (w/w):

| | |
|---|---|
| resveratrol | 10.12% |
| calcium lignin sulfonate | 57.31% |
| sucrose | 25.93% |
| water | 6.64% |

The following Examples illustrate the use of resveratrol CWS in beverages.

EXAMPLE 9

Near Water Beverage with Resveratrol CWS

| Ingredients | Weight (g) |
|---|---|
| Sucrose, fine crystalline | 7.20 |
| Citric acid 50% w/w | 2.00 |
| Potassium sorbate | 0.20 |
| Flavour ginger ale | 0.10 |
| Flavour lemon | 0.20 |
| Resveratrol CWS composition according to Example 6 | 0.703 |
| Fill with water to | 1000.00 |

Preparation:
Dissolve potassium sorbate in a small quantity of water.
Add citric acid solution, dry vitamin E 15% CC and resveratrol CWS.
Stir until all ingredients have dissolved.
Add sugar, stir again and add water to 1 liter.

Fill into appropriate packages and pasteurize or pasteurize and fill aseptically.

Over a period of 1 month no deposits or visible recrystallization could be detected. When crystalline resveratrol was used instead of the CWS form a deposit remained which could not be dissolved.

EXAMPLE 10

Soft Drink with Resveratrol CWS

| | Ingredients | Weight (g) |
|---|---|---|
| Bottling syrup | Sugar syrup 64°Brix | 156.2 |
| | Citric acid 50% w/w | 5.00 |
| | Potassium sorbate | 0.20 |
| | Ascorbic acid, fine powder | 0.30 |
| | Flavour | 0.50 |
| | Colour (beta-carotene 10% CWS as 1% solution)* | 6.00 |
| | Resveratrol CWS composition according to Example 6 | 0.703 |
| Add water to | | 1000 |

*Solution has to be prepared with water under stirring

Preparation:
Dissolve potassium sorbate in a part of water under stirring.
Add resveratrol CWS under further stirring.
Add sugar syrup, ascorbic acid, citric acid solution, water-soluble flavour and beta-carotene solution, one after the other, under stirring (no high-speed mixer).
Dilute the bottling syrup to one liter of beverage.
Fill into appropriate packages and pasteurize or pasteurize and fill aseptically.

Over a period of 1 month no deposits or visible recrystallization can be detected. When crystalline resveratrol is used instead of the CWS form a deposit remains which can not be dissolved.

EXAMPLE 11

Beverages with 10% juice and resveratrol CWS can be obtained as follows:

1) Juice Compound

| Ingredients | Weight [g] |
|---|---|
| Orange concentrate 60°Brix | 700.00 |
| Flavour (e.g. orange oil) | 3.7 |
| Beta-carotene 10% CWS | 1.13 |
| Water | 295.17 |

Preparation:
Disperse beta-carotene 10% CWS into water.
Mix orange concentrate with flavour oil and beta-carotene dispersion.
Pre-homogenize the mixture with a high speed mixer and homogenize using a high pressure homogenizer (1 minute, 150 bar/100 bar).

2) Beverage

|  |  | Weight [g] |
| --- | --- | --- |
| Bottling syrup | Sugar syrup 64°Brix | 156.20 |
|  | Potassium sorbate | 0.20 |
|  | Ascorbic acid, fine powder | 0.40 |
|  | Citric acid 50% w/w | 5.00 |
|  | Pectin 2% w/w solution | 10.00 |
|  | Juice compound (from 1) | 26.66 |
|  | Water soluble flavour | 0.30 |
|  | Water | 21.74 |
|  | Resveratrol (in CWS form) | 0.010-0.100 |
| Add water to |  | 1000 |

Preparation:
  Dissolve potassium sorbate into water under stirring.
  Add sugar syrup, ascorbic acid, citric acid, pectin, flavour/colour emulsion and resveratrol CWS to the potassium sorbate solution one after the other, under stirring (no high speed mixer).
  Fill 220 g of the bottling syrup to 1000 ml with water.
  Fill into appropriate packages and pasteurize or pasteurize and fill aseptically.
Alternatively Preparation Process:
  Add Resveratrol (in CWS form) in the juice compound (instead of in the bottling syrup): Mix resveratrol (in CWS form) to orange concentrate, flavour oil and beta-carotene dispersion. Note that In this case, the amount of resveratrol (in CWS form) has to be recalculated in order to obtain the same concentration in the final beverage. For example:

| Resveratrol (in CWS form) desired in the final beverage Concentration [g/l] | Resveratrol (in CWS form) If added in the bottling syrup Concentration [g/l] | Resveratrol (in CWS form) If added in the juice compound Concentration [g/l] |
| --- | --- | --- |
| 0.010 | 0.010 | 0.38 |
| 0.100 | 0.100 | 3.76 |

If resveratrol (in CWS form) is added to the juice compound, the quantity of the other ingredients will be unchanged excepting the quantity of water (water is added to 1000 ml). The bottling syrup preparation will be the same, excluding the addition of resveratrol (in CWS form).

The following Examples illustrate how resveratrol CWS can be used in the preparation of tablet formulations.

EXAMPLE 12

Straight Tablets 422 g of resveratrol CWS composition according to Example 1, 760 g of Avicel pH 102 (microcryst. cellulose), 6 g of Polyplasdone XL 10 (Crospovidone NF) and 4 g of Aerosil 200 (SiO$_2$) are sieved through a 1 mm sieve and mixed for 10 minutes in a tumbler mixer. 8 g of Mg-stearate are added and mixed for 2 minutes with the above mentioned ingredients. The mixture is compressed to tablets on a single punch press.
Tablet press: Korsch XP 1
Punch: 21×8.8 mm
Compression force: 15-20 KN Characterization of Tablets:
Tablet weight: 1200 mg
Content of resveratrol: 42 mg

EXAMPLE 13

Multivitamin Tablets

| 1. Vitamin B12 0.1% WS N | 6.00 g |
| --- | --- |
| 2. Dry Vitamin K1 5% S | 0.50 g |
| 3. Thiamine Mononitrate | 1.85 g |
| 4. Riboflavin TG | 1.70 g |
| 5. Dry Vitamin D3, Type 100 CWS/AM | 4.00 g |
| 6. 1% trituration of Biotin on maltodextrine | 3.00 g |
| 7. 10% trituration of folic acid on maltodextrine | 4.00 g |
| 8. Pyridoxine HCl | 2.44 g |
| 9. BetaTab 20% S | 6.00 g |
| 10. Dry vitamin A acetate 500 | 6.00 g |
| 11. Ascorbic acid 90% granulation | 67.00 g |
| 12. Dry vitamin E 75 HP | 40.00 g |
| 13. Niacinamide | 20.00 g |
| 14. Calcium-D-pantothenate | 10.90 g |
| 15. Resveratrol CWS composition according to Example 2 | 409.00 g |
| 16. Polyplasdone XL 10 (Crospovidone NF) | 7.00 g |
| 17. Aerosil 200 (SiO$_2$) | 4.00 g |
| 18. Avicel pH 102 (microcryst. cellulose) | 348.61 g |
| 19. Dibasic calcium phosphate | 550.00 g |
| 20. Mg-stearate | add 1500.00 g |

Components 1-10, 16 and 17 are sieved through a 1 mm sieve and mixed for 10 minutes in a tumbler mixer. Then components 11-15 and 18-19 are sieved, added and mixed with the other ingredients for 10 minutes. After addition of Mg-stearate the powder mix is again mixed for 2 minutes. The mixture is compressed to tablets on a single punch press.
Tablet press: Korsch XP 1
Punch: 22×9 mm oblong
Compression force: 15-20 kN
Characterization of Tablets (Tablet Weight: 1500 mg):

| Resveratrol | 47 mg |
| --- | --- |
| Vitamin B12 | 6 µg |
| Vitamin K1 | 25 µg |
| Vitamin B1 | 1.5 mg |
| Vitamin B2 | 1.7 mg |
| Vitamin D3 | 400 IU |
| Biotin | 30 µg |
| Folic acid | 400 µg |
| Vitamin B6 | 2 mg |
| Beta-carotene | 1.2 mg |
| Vitamin A | 3000 IU |
| Vitamin C | 60 mg |
| Vitamin E | 30 IU |
| Niacinamide | 20 mg |
| Pantothenic acid | 10 mg |

EXAMPLE 14

Multivitamin Effervescents

| 1. Vitamin B12 0.1% WS N | 6.00 g |
| --- | --- |
| 2. Dry vitamin K1 5% SD | 0.50 g |
| 3. Thiamine mononitrate | 1.85 g |
| 4. Riboflavin-5-phosphate sodium | 1.95 g |
| 5. Dry vitamin D3, type 100 CWS/AM | 2.00 g |
| 6. 1% Trituration of biotin on maltodextrine | 3.00 g |
| 7. 10% Trituration of folic acid on maltodextrine | 4.00 g |

-continued

| | | |
|---|---|---|
| 8. Pyridoxine HCl | 2.44 | g |
| 9. BetaTab 20% S | 6.00 | g |
| 10. Dry vitamin A palmitate type 250 CWS/F | 6.66 | g |
| 11. Ascorbic acid 90% granulation | 67.00 | g |
| 12. Dry vitamin E 50% CWS/F | 24.00 | g |
| 13. Niacinamide | 20.00 | g |
| 14. Calcium-D-pantothenate | 10.90 | g |
| 15. Resveratrol CWS composition according to Example 5 | 240.00 | g |
| 16. Citric acid fine granula | 1600.00 | g |
| 17. Sodium bicarbonate | 800.00 | g |
| 18. Mango flavor | 75.00 | g |
| 19. Aspartame | 45.00 | g |
| 20. Acesulfam | 15.00 | g |
| 21. Mannitol | 628.20 | g |
| 22. Sorbitol | 433.00 | g |
| 23. PEG | 7.50 | g |

Components 1-14 and 18-20 are passed through a 1 mm sieve and mixed for 15 minutes on a tumbler mixer. Then component 15 is passed through a 1 mm sieve, added together with components 16-17 and 21-23 to the above mixture and mixed again for 15 minutes. This mixture is compressed to effervescents on a single punch press.

Tablet press: Korsch XP 1
Punch: 25 mm
Compression force: 40-45 kN
Characterization of Tablets (Tablet Weight 4000 mg):

| | | |
|---|---|---|
| Resveratrol | 12 | mg |
| Vitamin B12 | 6 | µg |
| Vitamin K1 | 25 | µg |
| Vitamin B1 | 1.5 | mg |
| Vitamin B2 | 1.43 | mg |
| Vitamin D3 | 200 | IU |
| Biotin | 30 | µg |
| Folic acid | 400 | µg |
| Vitamin B6 | 2 | mg |
| Beta-carotene | 1.2 | mg |
| Vitamin A | 1666 | IU |
| Vitamin C | 60 | mg |
| Vitamin E | 12 | IU |
| Niacinamide | 20 | Mg |
| Pantothenic acid | 10 | Mg |

The invention claimed is:

1. An aqueous resveratrol-containing suspension comprising resveratrol particles suspended in an aqueous solution comprised of a protective colloid and sugar, wherein the protective colloid is selected from the group consisting of gelatines, ligninsulfonates or modified food starches, and wherein the suspension is wet-milled by a ball mill to yield an average particle size of the resveratrol particles of between 0.05 and 2 microns and a solubility of the resveratrol particles of about 100 mb/l or higher when suspended in a cold solution having a temperature between 5° C. to 25° C.

2. The aqueous resveratrol-containing suspension of claim 1, further comprising at least one additional component selected from the group consisting of artificial sweeteners, antioxidants, flavourings, polyethylene glycol, effervescent powders, excipients and adjuvants.

3. The aqueous resveratrol-containing suspension of claim 1, wherein resveratrol particles are present in an amount of 1-80 weight-%.

4. The aqueous resveratrol-containing suspension of claim 1, wherein the protective colloid is present in an amount of 20-99 weight-%.

5. A water-based food product which comprises the aqueous resveratrol-containing suspension as claimed in claim 1.

6. The water-based food product as in claim 5, wherein the food product is a beverage.

7. The method of claim 5, wherein the resveratrol-containing suspension is stably suspended in the food for at least 6 months.

8. A method of stably incorporating resveratrol into a water-based food, wherein the method comprises adding to the food a resveratrol-containing suspension as claimed in claim 1 at a stage of a production process for the food, and distributing the suspension in the food to form a homogeneous suspension therein.

9. A water-based food stably supplemented with the resveratrol-containing suspension as claimed in claim 1.

10. A beverage stably supplemented with the resveratrol-containing suspension as claimed in claim 1.

11. A process for preparing a resveratrol-containing suspension comprising the steps of:
(a) preparing an aqueous solution of a sugar and a protective colloid by dissolving the sugar and the protective colloid in deionized water, wherein the protective colloid is selected from the group consisting of gelatines, ligninsulfonates and modified food starches;
(b) adding resveratrol to the aqueous solution;
(c) stirring the resveratrol and aqueous solution to obtain an aqueous resveratrol-containing suspension; and thereafter
(d) wet-milling the stirred resveratrol-containing suspension for 1 to 6 hours by a ball mill to yield an average particle size of resveratrol in the aqueous suspension of between 0.05 and 2 microns.

12. The process according to claim 11, wherein step (d) is practiced to obtain an average particle size of the resveratrol in the suspension of between 0.1 and 1 microns.

13. The process according to claim 11, further comprising adding an antioxidant with resveratrol according to step (b) or after wet-milling according to step (d).

14. The process according to claim 11, wherein the protective colloid is octenyl succinic acid anhydride modified starch.

15. A process for preparing a dry powder composition comprising the steps of:
i) preparing an aqueous resveratrol-containing suspension according claim 11;
ii) spray-drying of the aqueous resveratrol-containing suspension.

16. A composition comprised of a suspension prepared according to the process of claim 11.

17. The composition of claim 16, which comprises resveratrol in an amount of 1-80 weight-%.

18. The composition of claim 16, which comprises resveratrol in an amount of 5-20 weight-%.

19. The composition of claim 16, which comprises the protective colloid in an amount of 20-99 weight-%.

20. The composition of claim 16, which comprises the protective colloid in an amount of 80-95 weight-%.

* * * * *